United States Patent
Laura Lapoint et al.

(10) Patent No.: US 10,512,428 B2
(45) Date of Patent: Dec. 24, 2019

(54) SYSTEM AND METHOD FOR FACILITATING SLEEP STAGE TRANSITIONS

(71) Applicant: KONINKLIJKE PHILIPS N.V., Eindhoven (NL)

(72) Inventors: Manuel Laura Lapoint, Pittsburgh, PA (US); Gary Nelson Garcia Molina, Madison, WI (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 793 days.

(21) Appl. No.: 15/100,435

(22) PCT Filed: Nov. 27, 2014

(86) PCT No.: PCT/IB2014/066373
§ 371 (c)(1),
(2) Date: May 31, 2016

(87) PCT Pub. No.: WO2015/087188
PCT Pub. Date: Jun. 18, 2015

(65) Prior Publication Data
US 2016/0302718 A1 Oct. 20, 2016

Related U.S. Application Data

(60) Provisional application No. 61/914,989, filed on Dec. 12, 2013.

(51) Int. Cl.
*A61B 5/00* (2006.01)
*A61B 5/024* (2006.01)
(Continued)

(52) U.S. Cl.
CPC ........ *A61B 5/4812* (2013.01); *A61B 5/02438* (2013.01); *A61B 5/04012* (2013.01);
(Continued)

(58) Field of Classification Search
CPC .................. A61M 21/02; A61M 21/00; A61M 2021/0005; A61M 2021/0022;
(Continued)

(56) References Cited

U.S. PATENT DOCUMENTS

| 6,052,619 A | 4/2000 | John |
| 7,041,049 B1 * | 5/2006 | Raniere ................. A61M 21/02 128/905 |

(Continued)

FOREIGN PATENT DOCUMENTS

| CN | 101243973 A | 8/2008 |
| CN | 103239227 A | 8/2013 |

(Continued)

OTHER PUBLICATIONS

Cirelli et al, "Is Sleep Essential?", PLoS Biology, vol. 6 Issue 8, 2008, pp. 1605-1611.
(Continued)

*Primary Examiner* — Samuel G Gilbert (57) ABSTRACT

The present disclosure pertains to a system that facilitates transitions between sleep states and/or stages during a sleep session of a subject. The system facilitates transitions between sleep states and/or stages by monitoring the brain activity of a subject and providing sensory stimulation to guide brain activity parameters into target ranges. The system includes one or more of a sensory stimulator, a sensor, a processor, electronic storage, a user interface, and/or other components.

21 Claims, 4 Drawing Sheets

(51) Int. Cl.
*A61B 5/0476* (2006.01)
*A61B 5/0482* (2006.01)
*A61M 21/02* (2006.01)
*A61B 5/04* (2006.01)
*A61B 5/11* (2006.01)
*A61B 8/08* (2006.01)
*A61B 5/08* (2006.01)
*A61M 21/00* (2006.01)

(52) U.S. Cl.
CPC ......... *A61B 5/0476* (2013.01); *A61B 5/0482* (2013.01); *A61B 5/11* (2013.01); *A61B 8/08* (2013.01); *A61M 21/02* (2013.01); *A61B 5/0816* (2013.01); *A61B 5/1118* (2013.01); *A61B 5/7285* (2013.01); *A61M 2021/0016* (2013.01); *A61M 2021/0022* (2013.01); *A61M 2021/0027* (2013.01); *A61M 2021/0044* (2013.01); *A61M 2021/0055* (2013.01); *A61M 2205/502* (2013.01); *A61M 2205/52* (2013.01); *A61M 2230/04* (2013.01); *A61M 2230/10* (2013.01); *A61M 2230/40* (2013.01); *A61M 2230/63* (2013.01)

(58) Field of Classification Search
CPC .. A61M 2021/0044; A61M 2021/0055; A61M 2021/0061
USPC .................................................. 600/26–28
See application file for complete search history.

(56) References Cited

U.S. PATENT DOCUMENTS

| | | | | |
|---|---|---|---|---|
| 8,784,293 | B2* | 7/2014 | Berka | A61M 21/02 600/26 |
| 2008/0081941 | A1 | 4/2008 | Tononi | |
| 2008/0319505 | A1 | 12/2008 | Boyden et al. | |
| 2010/0087701 | A1* | 4/2010 | Berka | A61M 21/02 600/27 |
| 2012/0296390 | A1 | 11/2012 | Nakashima et al. | |
| 2013/0035541 | A1 | 2/2013 | Kashima et al. | |
| 2013/0303837 | A1 | 11/2013 | Berka et al. | |

FOREIGN PATENT DOCUMENTS

| | | |
|---|---|---|
| CN | 103372258 A | 10/2013 |
| JP | 2000116785 A | 4/2000 |
| WO | 2005055802 A2 | 6/2005 |
| WO | 2014170781 A1 | 10/2014 |

OTHER PUBLICATIONS

Tononi et al., "Sleep Function and Synaptic Homeostasis", Sleep Medicine Reviews, vol. 10, Issue 1, 2006, pp. 49-62.

Iber et al, "The AASM Manual for the Scoring of Sleep and Associated Events", First American Academy of Sleep Medicine, 2007, pp. 3-59.

Ngo et al, "Induction of Slow Oscillations by Rhythmic Acoustic Stimulation", Journal of Sleep Research, vol. 22, 2012, pp. 22-31.

Huang et al, "A Comprehensive Review of the Psychological Effects of Brainwave Entrainment", Alternative Therapies in Health and Medicine, vol. 14, No. 5, 2008, pp. 38-50.

Marshall et al, "Boosting Slow Oscillations During Sleelp Potentiates Memory", Nature, vol. 44, 2006, pp. 610-613.

Lim et al, "'Eyes-Closed' SSVEP-Based BCI for Binary Communication of Individuals With Impaired Oculomotor Function", International Winter Workskhop on Brain-Computer Interface (BC), 20123, pp. 79-80.

Marshall et al, "Transcranial Direct Current Stimulation During Sleep Improves Declarative Memory", The Journal of Neuroscience, vol. 24, No. 44, 2004, pp. 9985-9992.

Massimini et al, "Triggering Sleep Slow Waves by Transcranial Magnetic Stimulation", PNAS, vol. 104, No. 20, 2007, pp. 8496-8501.

Riedner et al, "Temporal Dynamics of Cortical Sources Underlying Spontaneous and Peripherally Evoked Slow Waves", Progress in Brain Research, vol. 193, 2011, pp. 201-218.

Cottone et al, "The Effect of Unilateral Somatosensory Stimulation Onhimspheric Asymmetries During Slow Wave Sleep", Sleep, vol. 27, No. 1, 2004, pp. 63-68.

* cited by examiner

SYSTEM AND METHOD FOR FACILITATING SLEEP STAGE TRANSITIONS

CROSS-REFERENCE TO PRIOR APPLICATIONS

This application is the U.S. National Phase application under 35 U.S.C. § 371 of International Application Serial No. PCT/IB32014/066373, filed on Nov. 27, 2014, which claims the benefit of U.S. Application Ser. No. 61/914,989, filed on Dec. 12, 2013. These applications are hereby incorporated by reference herein.

BACKGROUND

1. Field

The present disclosure pertains to a system and method for manipulating electrical activity in the brain of a subject to facilitate sleep stage transitions during a sleep session.

2. Description of the Related Art

Systems for monitoring sleep are known. Sensory stimulation during sleep is known. Sensory stimulation during sleep is often applied continuously and/or at intervals that do not aim at influencing the sleeping patterns of a subject to cause sleep stage transitions. The present disclosure overcomes deficiencies in prior art systems.

SUMMARY

Accordingly, one or more aspects of the present disclosure relate to a system configured to facilitate transitions between sleep stages during a sleep session of a subject. The system comprises one or more sensory stimulators, one or more sensors, one or more physical computer processors, and/or other components. The one or more sensory stimulators are configured to provide sensory stimuli to the subject during the sleep session. The one or more sensors are configured to generate output signals conveying information related to brain activity of the subject. The one or more physical computer processors are configured, by computer readable instructions, to determine one or more brain activity parameters of the subject based on the output signals; determine target ranges for the one or more brain activity parameters, the target ranges determined based on one or more of previous sleep sessions of the subject or information received from a user; compare a given brain activity parameter to a corresponding target range; and control the sensory stimulators to provide sensory stimulation to the subject to guide the brain activity parameters of the subject into the target ranges such that, responsive to the given brain activity parameter being outside the corresponding target range, the control component controls the sensory stimulators to provide sensory stimulation to the subject to guide the given brain activity parameter into the corresponding target range.

Another aspect of the present disclosure relates to a method for facilitating transitions between sleep stages during a sleep session of a subject with a facilitation system. The system comprises one or more sensory stimulators, one or more sensors, one or more physical computer processors, and/or other components. The method comprises generating output signals conveying information related to brain activity of the subject with the one or more sensors; determining one or more brain activity parameters of the subject based on the output signals with the one or more physical computer processors; determining target ranges for the one or more brain activity parameters with the one or more physical computer processors, the target ranges determined based on one or more of previous sleep sessions of the subject or information received from a user; comparing a given brain activity parameter to a corresponding target range with the one or more physical computer processors; and controlling the sensory stimulators to provide sensory stimulation to the subject to guide the brain activity parameters of the subject into the target ranges such that, responsive to the given brain activity parameter being outside the corresponding target range, the sensory stimulators are controlled to provide sensory stimulation to the subject to guide the given brain activity parameter into the corresponding target range.

Still another aspect of present disclosure relates to a system configured to facilitate transitions between sleep stages during a sleep session of a subject. The system comprises means for providing sensory stimuli to the subject during the sleep session; means for generating output signals conveying information related to brain activity of the subject; means for determining one or more brain activity parameters of the subject based on the output signals; means for determining target ranges for the one or more brain activity parameters, the target ranges determined based on one or more of previous sleep sessions of the subject or information received from a user; means for comparing a given brain activity parameter to a corresponding target range; and means for controlling the sensory stimulators to provide sensory stimulation to the subject to guide the brain activity parameters of the subject into the target ranges such that, responsive to the given brain activity parameter being outside the corresponding target range, the means for controlling controls the means for providing to provide sensory stimulation to the subject to guide the given brain activity parameter into the corresponding target range.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
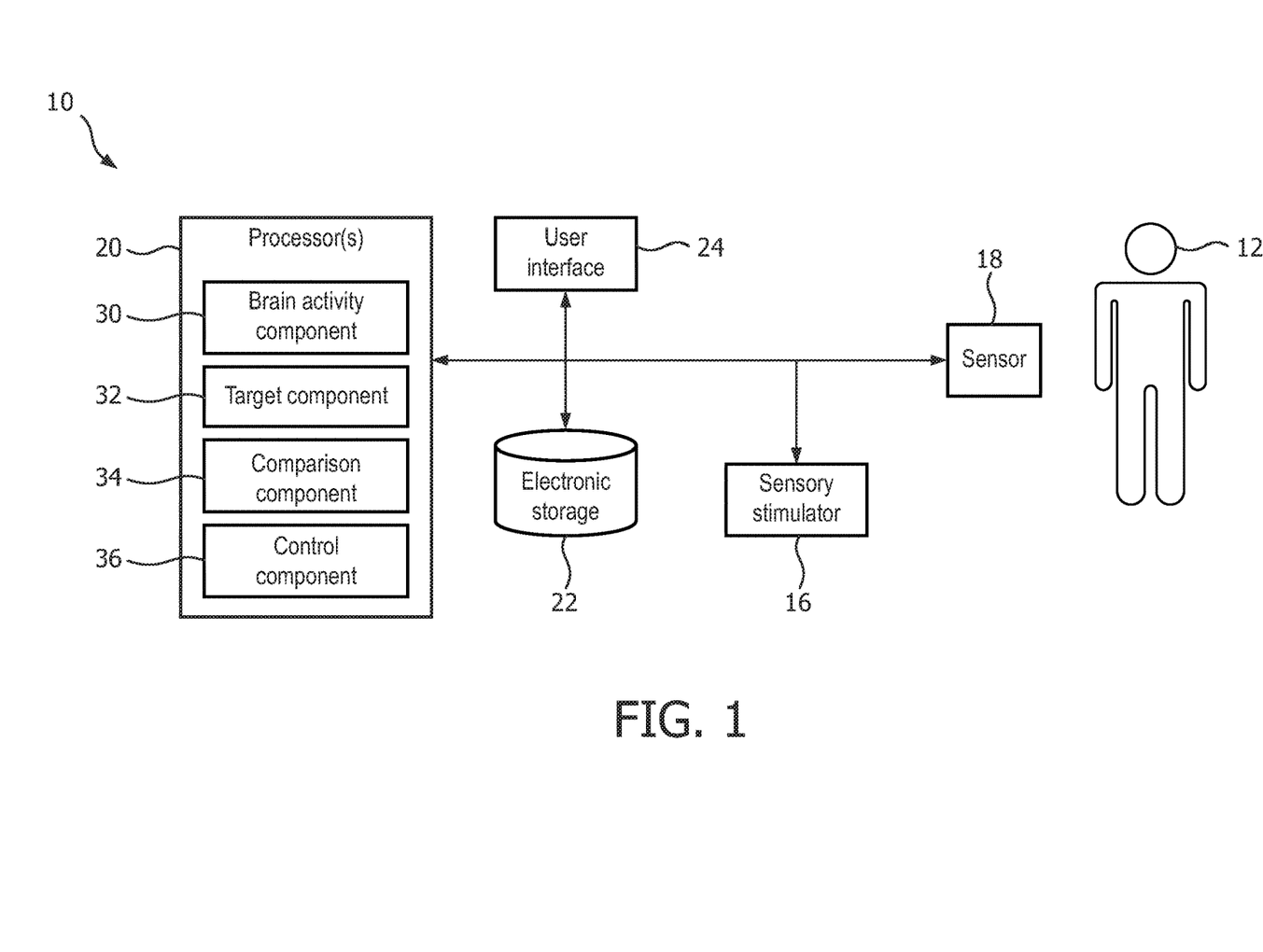
FIG. 1 is a schematic illustration of a system configured to facilitate transitions between sleep states during a sleep session of a subject.

FIG. 1 is a schematic illustration of a system 10 configured to facilitate transitions between sleep states during a sleep session of a subject 12. In some embodiments, transitioning between sleep states corresponds to transitioning between sleep stages (e.g., standard sleep stages such as N1, N2, N3, REM). In some embodiments, system 10 is configured such that sleep states do not correspond to standard sleep stages. System 10 is configured to facilitate transitions between sleep states and/or stages by monitoring the brain activity of subject 12 and providing sensory stimulation to subject 12 to guide brain activity parameters into target ranges. In system 10, brain activity information generated by sensors is used to control sensory stimulation. Advantages of system 10 include the fact that stimulation can be appropriately timed. For example, using system 10, stimulation is delivered at an appropriate time in order to avoid interfering with the subject's falling asleep process and/or to induce the subject to wake up at a pre-determined time. In some embodiments, system 10 includes one or more of a sensory stimulator 16, a sensor 18, a processor 20, electronic storage 22, a user interface 24, and/or other components.

Sensory stimulator 16 is configured to provide sensory stimuli to subject 12. Sensory stimulator 16 is configured to provide sensory stimulation to subject 12 prior to a sleep session, during a sleep session, and/or at other times. For example, sensory stimulator 16 may be configured to provide sensory stimuli to subject 12 during deep (e.g., slow wave sleep) sleep in a sleep session to facilitate a transition to a lighter stage of sleep. As another example, sensory stimulator 16 may be configured to provide sensory stimulation to subject 12 to induce deeper sleep in subject 12 (e.g., facilitate a transition from a lighter stage of sleep). In some embodiments, sensory stimulator 16 may be configured such that facilitating a transition between sleep stages includes inducing, increasing, enhancing, and/or decreasing sleep slow waves in subject 12.

Sensory stimulator 16 is configured to facilitate transitions between sleep stages through non-invasive brain stimulation and/or other methods. Sensory stimulator 16 may be configured to facilitate transitions between sleep stages through non-invasive brain stimulation using sensory stimuli. The sensory stimuli include odors, sounds, visual stimulation, touches, tastes, somato-sensory stimulation, haptic, and/or other stimuli. For example, acoustic tones may be provided to subject 12 to facilitate a transition from a lighter stage of sleep to a deeper stage of sleep. Examples of sensory stimulator 16 may include one or more of a music player, a tone generator, a collection of electrodes on the scalp of subject 12, a unit to deliver vibratory stimulation, a coil generating a magnetic field to directly stimulate the brain's cortex, light generators, a fragrance dispenser, and/or other devices. In some embodiments, sensory stimulator 16 is configured to adjust the intensity of the stimulation provided to subject 12.

Sensor 18 is configured to generate output signals conveying information related to brain activity of subject 12. The brain activity of subject 12 may correspond to a current sleep stage of subject 12. The current sleep stage of subject 12 may be associated with rapid eye movement (REM) sleep, non-rapid eye movement (NREM) sleep, and/or other sleep. The current sleep stage of subject 12 may be one or more of NREM stage N1, stage N2, or stage N3 sleep, REM sleep, and/or other sleep stages. In some embodiments, NREM stage 3 or stage 2 sleep may be slow wave (e.g., deep) sleep. Sensor 18 may comprise one or more sensors that measure such parameters directly. For example, sensor 18 may include electroencephalogram (EEG) electrodes configured to detect electrical activity along the scalp of subject 12 resulting from current flows within the brain of subject 12. Sensor 18 may comprise one or more sensors that generate output signals conveying information related to brain activity of subject 12 indirectly. For example, one or more sensors 18 may generate an output based on a heart rate of subject 12 (e.g., sensor 18 may be a heart rate sensor located on the chest of subject 12, and/or be configured as a bracelet on a wrist of subject 12, and/or be located on another limb of subject 12), movement of subject 12 (e.g., sensor 18 may include a bracelet around the wrist and/or ankle of subject 12 with an accelerometer such that sleep may be analyzed using actigraphy signals), respiration of subject 12, and/or other characteristics of subject 12. Although sensor 18 is illustrated at a single location near subject 12, this is not intended to be limiting. Sensor 18 may include sensors disposed in a plurality of locations, such as for example, within (or in communication with) sensory stimulator 16, coupled (in a removable manner) with clothing of subject 12, worn by subject 12 (e.g., as a headband, wristband, etc.), positioned to point at subject 12 while subject 12 sleeps (e.g., a camera that conveys output signals related to movement of subject 12), and/or in other locations.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensory stimulator 16), or processor 20 may represent processing functionality of a plurality of devices operating in coordination.

As shown in FIG. 1, processor 20 is configured to execute one or more computer program components. The one or more computer program components may comprise one or more of a brain activity component 30, a target component 32, a comparison component 34, a control component 36, and/or other components. Processor 20 may be configured to execute components 30, 32, 34, and/or 36 by software; hardware; firmware; some combination of software, hardware, and/or firmware; and/or other mechanisms for configuring processing capabilities on processor 20.

It should be appreciated that although components 30, 32, 34, and 36 are illustrated in FIG. 1 as being co-located within a single processing unit, in embodiments in which processor 20 comprises multiple processing units, one or more of components 30, 32, 34, and/or 36 may be located remotely from the other components. The description of the functionality provided by the different components 30, 32, 34, and/or 36 described below is for illustrative purposes, and is not intended to be limiting, as any of components 30, 32, 34, and/or 36 may provide more or less functionality than is described. For example, one or more of components 30, 32, 34, and/or 36 may be eliminated, and some or all of its functionality may be provided by other components 30, 32, 34, and/or 36. As another example, processor 20 may be configured to execute one or more additional components that may perform some or all of the functionality attributed below to one of components 30, 32, 34, and/or 36.

Brain activity component 30 is configured to determine one or more brain activity parameters of subject 12. Brain activity component 30 is configured to determine one or more brain activity parameters based on the output signals from sensor 18. In some embodiments, determining one or more brain activity parameters may include generating and/or monitoring an electroencephalogram (EEG) during a sleep session of subject 12. The EEG may be displayed, for example, by user interface 24. In some embodiments, brain activity component 30 is configured such that the one or more brain activity parameters are and/or are related to a frequency, amplitude, phase, presence of specific sleep patterns such as spindles, K-complexes, or sleep slow waves, alpha waves, and/or other characteristics of an EEG signal. In some embodiments, the one or more brain activity parameters are determined based on the frequency, amplitude, and/or other characteristics of the EEG signal. In some embodiments, the determined brain activity parameters and/or the characteristics of the EEG may be and/or indicate sleep states that correspond to the REM and/or NREM sleep stages described above. In some embodiments, the determined brain activity parameters are the REM and/or NREM sleep stages described above.

For example, typical EEG characteristics during NREM sleep include a transition from alpha waves (e.g., about 8-12 Hz) to theta waves (e.g., about 4-7 Hz) for sleep stage N1; presence of sleep spindles (e.g., about 11 to 16 Hz) and/or K-complexes (e.g., similar to sleep slow waves) for sleep stage N2; presence of delta waves (e.g., about 0.5 to 2 Hz), also known as sleep slow waves, with peak-to-peak amplitudes greater than about 75 uV for sleep stage N3; and/or other characteristics. The determined brain activity parameters may be the sleep stages themselves. The determined brain activity parameters may be sleep states such as light REM sleep, deep NREM sleep, and/or other sleep stages. Light NREM sleep may be a sleep state characterized by the fact that the alpha activity (e.g., EEG power in the 8-12 Hz band) is no longer present and slow wave activity is not yet present. In addition, spindle activity (EEG power in the 11 to 16 Hz band) may be high. Deep NREM sleep may be characterized by the fact that delta activity (e.g., EEG power in the 0 to 4 Hz band) is dominant.

Figure 2:
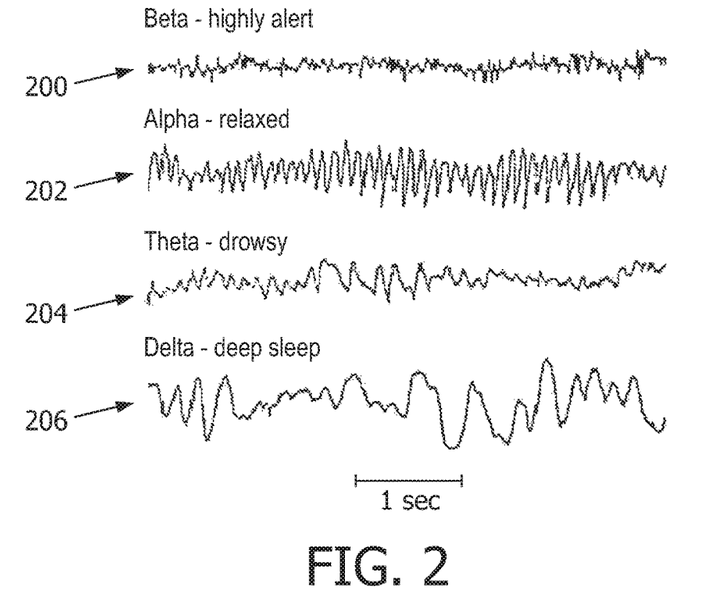
FIG. 2 illustrates EEG signals for different levels of alertness.

FIG. 2 illustrates EEG signals (e.g., frequency patterns) for different levels of alertness. As described above, correlation exists between the EEG patterns and sleep states and/or stages. FIG. 2 illustrates beta waves 200, alpha waves 202, theta waves 204, and delta waves 206. Beta waves 200 indicate a high level of alertness in a subject. Alpha waves 202 indicate relaxation. Theta waves 204 indicate drowsiness. Delta waves 206 indicate deep sleep.

Returning to FIG. 1, target component 32 is configured to determine target ranges for the one or more brain activity parameters. In some embodiments, target component 32 is configured to obtain target sleep state and/or stage information and determine the target ranges for the brain activity parameters based on the obtained target information. Obtaining the target sleep state and/or stage information for the brain activity parameters includes receiving the information via user interface 24, determining the information based on previous sleep sessions of subject 12, determining the information based on previous sleep sessions of a population of subjects that are related to subject 12, receiving the information from external computing systems (e.g., an alarm clock wakeup system), obtaining information determined at manufacture, and/or obtaining the information by other methods. The obtained target sleep stage and/or state information may include information related to a target EEG frequency, a target sleep stage, a target density of sleep slow waves (e.g., at least six sleep slow waves in the next 30 seconds which is the criterion used in manual scoring to categorize a 30 second long EEG segment as belonging to N3, for example), a percentage of alpha activity, and/or other target information. In some embodiments, determining target ranges includes determining one or more threshold values for a given brain activity parameter that define a target range for that parameter. The threshold values are determined based on the obtained target information.

For example, while subject 12 is determined to be in stage N2 sleep by brain activity component 30, a user (e.g., a doctor, a nurse, a relative, a friend, a caregiver, etc.) may enter and/or select sleep stage N3 via user interface 24 as a target sleep stage because they want subject 12 to experience deep sleep. Target component 32 may determine the target range (including one or more threshold values) for one or more brain activity parameters that, once within the target range, would indicate a transition to stage N3 sleep by subject 12. As another example, while the frequency of the EEG signal for subject 12 is determined to be about 4-7 Hz (theta waves) by brain activity component 30, an external alarm clock system communicates a target frequency range of 15-30 Hz (beta waves) to system 10 because subject 12 is supposed to wake up in 30 minutes. Target component 32 may determine a target range of 15-30 Hz based on the information received from the external alarm clock system. A user may include subject 12 in such embodiments (and/or other embodiments) because system 10 is configured such that subject 12 may set (e.g., via user interface 24) his own wake up time and/or sleep state targets prior to going to sleep.

Comparison component 34 is configured to compare the one or more brain activity parameters to the target ranges. In some embodiments, comparing the one or more brain activity parameters to the target ranges includes comparing a given brain activity parameter to the one or more threshold values that define the target range. Comparison component 34 may determine whether the given brain activity parameter is in a target range based on whether the given brain activity parameter has breached one or more of the threshold values.

For example, target component 32 may determine that stage N3 is the target sleep stage for subject 12 based on input from a caregiver via user interface 24. Brain activity component 30 may determine that subject 12 is in stage N1 sleep based on a ratio of the power levels in the beta band and the delta band of the EEG and pre-programmed power level ratio thresholds (e.g., determined at manufacture) for individual sleep stages. Comparison component 34 may be configured to compare the current power level ratio determined by brain activity component 30 to the previously determined threshold ratios for stage N3 sleep.

In some embodiments, as described above, the one or more brain activity parameters may be one or more frequency characteristics of the EEG. This may provide a relatively simple quantification of the sleep state of subject 12 without reflecting and/or determining the sleep stages like in the example above. Comparison component 34 may be configured to determine the difference between the current sleep state of subject 12 and the desired sleep state of subject 12 based on the spectral difference between the current characteristics of the EEG and the target characteristics of the EEG (e.g., the target range).

Comparison component 34 may be configured to compare the one or more brain activity parameters to the target ranges one or more times during a sleep session. In some embodiments, comparison component 34 may be configured to compare the one or more brain activity parameters to the target ranges one or more times during a given period of time after target component 32 determines target ranges for the one or more brain activity parameters. In some embodiments, comparison component 34 may be configured to compare the one or more brain activity parameters to the target ranges continuously during the sleep session.

Control component 36 is configured to control sensory stimulator 16 to provide sensory stimulation to subject 12 to guide the brain activity parameters of subject 12 into the target ranges. Control component 36 is configured to control sensory stimulator 16 to provide sensory stimulation to subject 12 to guide the brain activity parameters of subject 12 into the target ranges responsive to the brain activity parameters of subject 12 being outside the target ranges.

Controlling sensory stimulator 16 includes determining a timing, a frequency, an intensity, and/or other parameters of the stimulation provided to subject 12. The timing, frequency, intensity, and/or other parameters of the stimulation provided to subject 12 may be controlled to increase and/or decrease sleep slow waves, for example, in subject 12 during the sleep session to facilitate transitions between sleep states and/or stages. The timing, frequency, intensity, and/or other parameter determinations are based on previous sleep sessions of subject 12, sleep sessions of a representative group of subjects related to subject 12, may be determined at manufacture, and/or determined by other methods.

Control component 36 is configured to control sensory stimulator 16 such that the timing of the sensory stimuli (e.g., auditory tones) comprises a regular, repeating interval of time between individual stimuli delivered to subject 12. In some embodiments, such as when system 10 is facilitating a transition from stage N2 to stage N3 sleep, control component 36 is configured such that the regular, repeating interval of time between individual stimuli (e.g., tones) is about 0.8 to about 1.5 seconds. This type of stimulation may influence the EEG by entraining the electrical activity of the brain of subject 12. The possibility of inducing electrical activity at higher, lower, and/or other timings, frequencies, and/or intensities of stimulation to facilitate transitions from N3 to N2, from N2 to N1, and/or between any other sleep stages is also contemplated. For example, in some embodiments, control component 36 is configured such that the timing of the sensory stimulation is variable between individual stimuli. In some embodiments, the sensory stimulation is tailored by control component 36 based on the information from sensor 18, brain activity component 30, target component 32, comparison component 34, and/or other sources. The sensory stimulation is tailored by control component 36 to entrain the EEG in the frequency band(s) where discrepancies (e.g., including both deficits and/or excess) exist between the brain activity parameter range for the target sleep state and the brain activity parameters for the current sleep state. In some embodiments, control component 36 is configured to control sensory stimulator 16 to provide a composite sensory stimulation (e.g., an additive combination of two or more sensory stimuli at different frequencies) so that the EEG exhibits oscillatory components at the individual frequencies of the combined stimuli. In some embodiments, given that the brain is a non-linear system, system 10 may be configured such that a user may cause stimulation to be delivered at two frequencies, $f_1$ and $f_2$ (e.g., generally higher than 60 Hz), which can produce EEG activity at the absolute value of the difference in the frequencies (abs(f1−f2)). The EEG bandwidth may be estimated to be up to 60-80 Hz. Using binaural beats, sound at 300 and/or 310 Hz may be used in order to evoke 10 Hz oscillatory activity, for example.

In some embodiments, control component 36 may control sensory stimulator 16 to provide the sensory stimulation during the sleep session such that the sensory stimulation does not unintentionally wake subject 12. Controlling sensory stimulator 16 to provide sensory stimulation so subject 12 is not unintentionally aroused from sleep may be accomplished by controlling the timing, frequency, intensity, and/or other parameters of the stimulation. For example, control component 36 may control sensory stimulator 16 to provide the sensory stimulation at a low intensity level when subject 12 is to remain asleep and at a high intensity level if subject 12 is to be aroused from deep sleep. As another example, control component 36 may cause sensory stimulator 16 to deliver acoustic stimulation to subject 12 to increase sleep slow waves just after subject 12 has fallen asleep, and not while subject 12 is falling asleep. Control component 36 may be configured such that the intensity of the sensory stimulation is adjusted based on the likelihood of producing arousals. Control component 36 is configured to determine the likelihood of producing arousals based on the instantaneous EEG power in the beta band, and/or by other methods.

Figure 3:
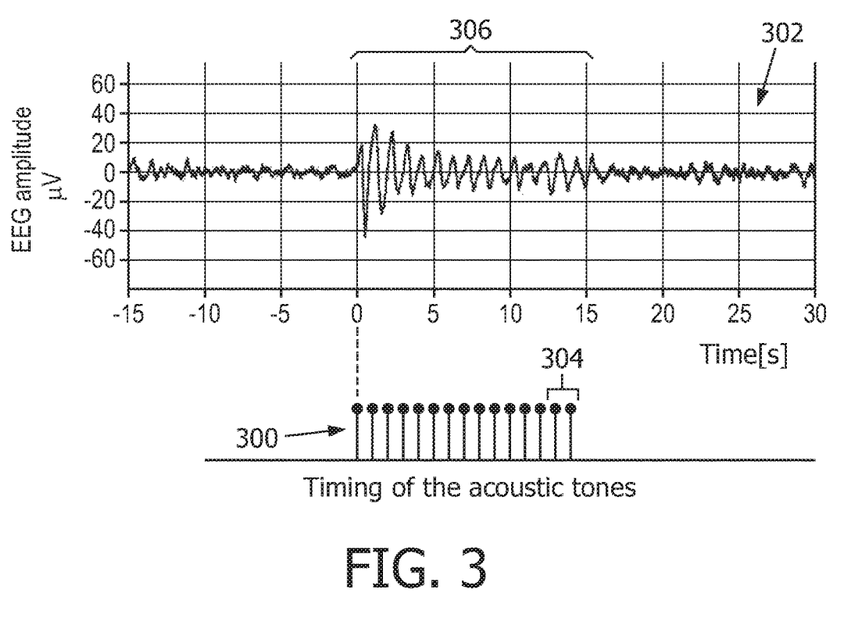
FIG. 3 illustrates a series of acoustic tones delivered as sensory stimulation.

FIG. 3 illustrates a series of acoustic tones 300 delivered as sensory stimulation. In this example, the tones 300 have a fixed inter tone interval 304 of about one second. As shown in FIG. 3, during sleep, the entrainment of brain activity through sensory stimulation occurs (which can be used to facilitate transitions between sleep stages, for example). FIG. 3 is an example of facilitating a transition to a deeper sleep stage. A segment 302 of EEG is represented which shows the presence of oscillatory activity 306 evoked (entrained) by a sequence of 50-millisecond long acoustic tones 300. In this example, the acoustic volume was set at a level sufficiently high to influence the EEG and sufficiently low so that the user (e.g., subject 12) would not be aroused. The entrained oscillations 306 are substantially identical to sleep slow waves and the presence of these slow waves brings similar benefits as the ones brought by spontaneous slow wave sleep. It should be noted that FIG. 3 illustrates a series of 15 acoustic tones 300. This is not intended to be limiting. The number of tones and/or other individual stimuli used for sensory stimulation may be determined by control component 36, set at manufacture, set and/or adjusted by a user via user interface 24, determined based on previous sleep sessions of subject 12, and/or determined by other methods. A user may include a doctor, a caregiver, subject 12, and/or other users.

Figure 4:
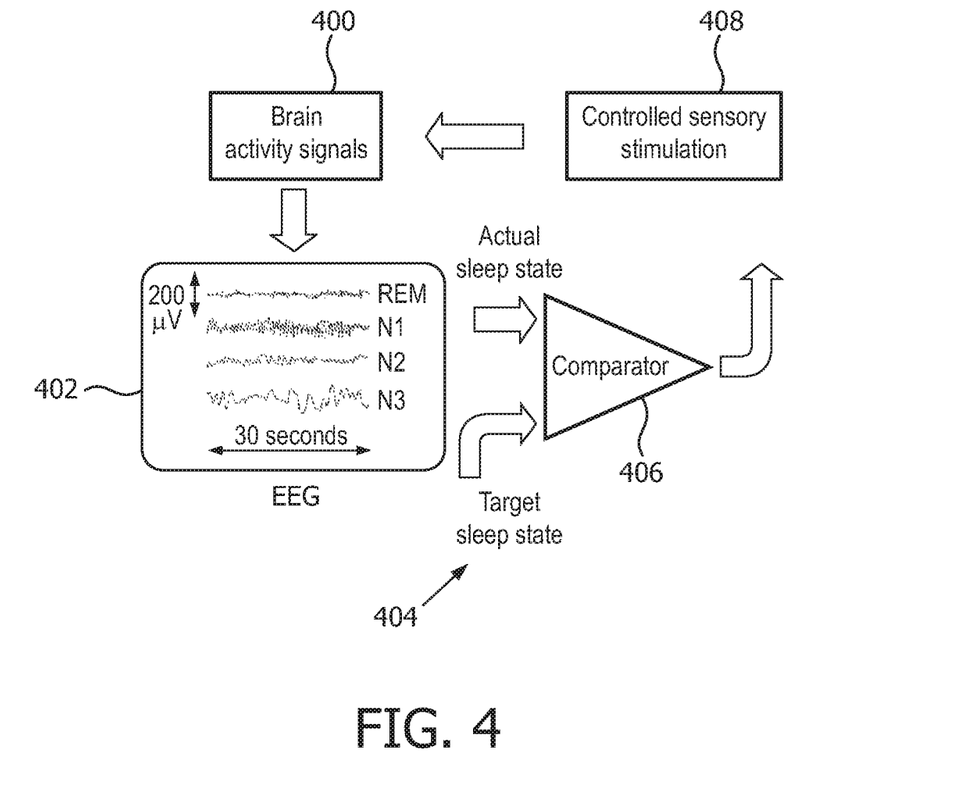
FIG. 4 is a schematic summary of manipulating electrical activity in the brain of a subject to facilitate sleep stage transitions during a sleep session.

FIG. 4 is a schematic summary of manipulating electrical activity in the brain of a subject (e.g., subject 12) to facilitate sleep stage transitions during a sleep session. At a step 400, output signals that convey information related to brain activity are generated. At a step 402 an EEG is generated and brain activity parameters are determined. The brain activity parameters are related to the frequency characteristics of the EEG as shown in FIG. 4. The brain activity parameters may correspond to one or more of the REM and/or NREM sleep stages discussed above. The brain activity parameters may be the current sleep stage of the subject. At a step 404, a target sleep state is determined. The target sleep state may be determined based on information received from a user via a user interface, for example. At a step 406 the actual sleep state is compared to the target sleep state. At a step 408, one or more sensory stimulators are controlled to provide sensory stimulation to the subject to guide the brain activity parameters of the subject into the target ranges. Sensory stimulators are controlled to provide sensory stimulation to the subject to guide the brain activity parameters of the subject into the target ranges responsive to the brain activity parameters of the subject being outside the target ranges. The process may repeat one or more times until the brain activity parameters of the subject are guided into the target ranges.

Returning to FIG. 1, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information determined by processor 20, information received via user interface 24 and/or external computing systems, and/or other information that enables system 10 to function properly. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and subject 12, and/or other users through which subject 12 and/or other users may provide information to and receive information from system 10 (e.g., a target sleep stage). This enables data, cues, results, and/or instructions and any other communicable items, collectively referred to as "information," to be communicated between a user (e.g., subject 12) and one or more of sensory stimulator 16, sensor 18, processor 20, and/or other components of system 10. For example, an EEG may be displayed to a caregiver via user interface 24.

Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with sensory stimulator 16 and/or other components of system 10.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

Figure 5:
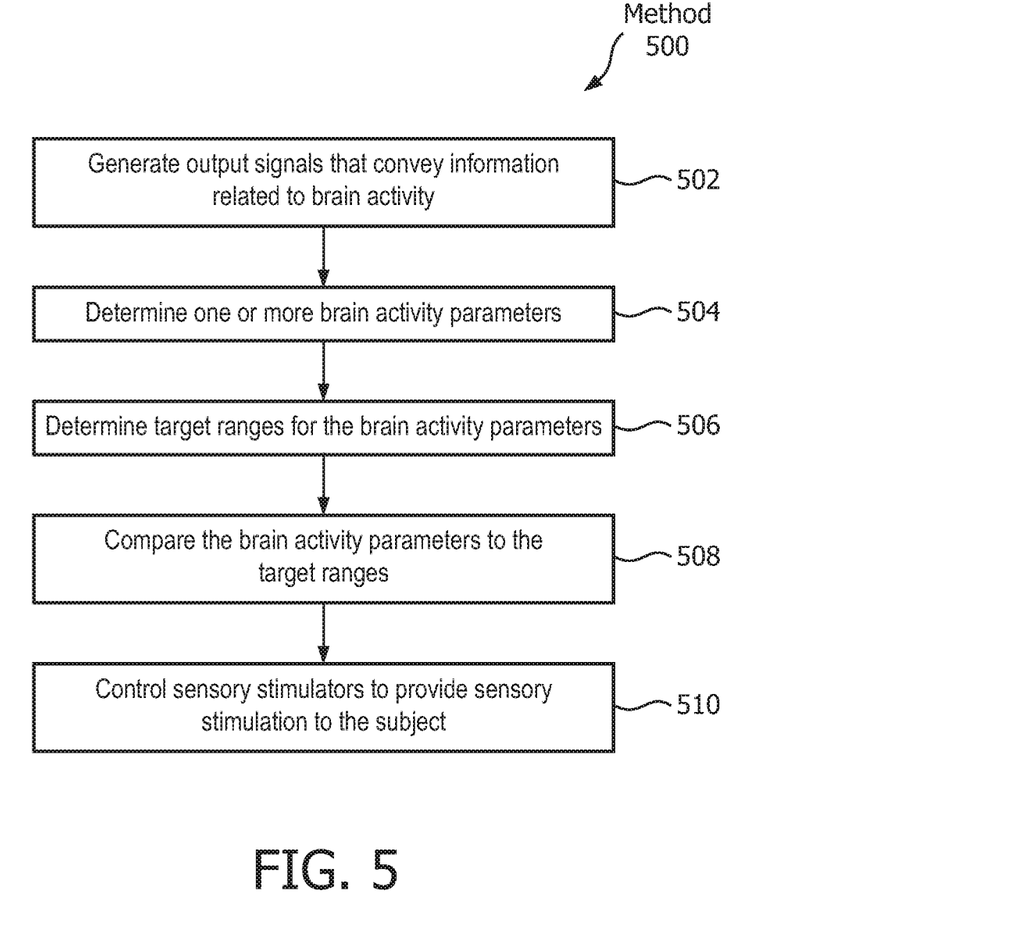
FIG. 5 illustrates a method for facilitating transitions between sleep stages during a sleep session of a subject with a facilitation system.

FIG. 5 illustrates a method 500 for facilitating transitions between sleep stages during a sleep session of a subject with a facilitation system. The system comprises one or more sensory stimulators, one or more sensors, one or more physical computer processors, and/or other components. The one or more physical computer processors are configured to execute computer program components. The computer program components comprise a brain activity component, a target component, a comparison component, a control component, and/or other components. The operations of method 500 presented below are intended to be illustrative. In some embodiments, method 500 may be accomplished with one or more additional operations not described, and/or without one or more of the operations discussed. Additionally, the order in which the operations of method 500 are illustrated in FIG. 5 and described below is not intended to be limiting.

In some embodiments, method 500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/or software to be specifically designed for execution of one or more of the operations of method 500.

At an operation 502, output signals conveying information related to brain activity are generated. In some embodiments, system 10 may be configured to generate an EEG based on the output signals. In some embodiments, operation 502 is performed by one or more sensors the same as or similar to sensors 18 (shown in FIG. 1 and described herein).

At an operation 504, one or more brain activity parameters are determined. In some embodiments, the brain activity parameters may be determined based on the EEG. The one or more brain activity parameters may be related to a frequency of the EEG. In some embodiments, operation 504 may include determining a current sleep stage of the subject. In some embodiments, operation 504 is performed by a processor component the same as or similar to brain activity component 30 (shown in FIG. 1 and described herein).

At an operation 506, target ranges for the brain activity parameters are determined. In some embodiments, the target ranges are determined based on the EEG. In some embodiments, operation 506 includes receiving a target sleep stage from a caregiver and determining the target ranges for the brain activity parameters based on the target sleep stage. In some embodiments, the target sleep stage is a lighter sleep stage relative to the current sleep stage of the subject. In some embodiments, the target sleep stage is a deeper sleep stage relative to the current sleep stage of the subject.

In some embodiments, operations 502-510 are repeated one or more times (e.g., iterated) until the brain activity parameters are within the target ranges. The target ranges may not be necessarily determined (operation 506) for individual iterations. For example, new target ranges may be determined only when the target ranges change due to internal and/or external factors (e.g., user input via the user interface). System 10 is configured to decrease the difference between the target ranges and current brain activity parameters (which are determined for the individual iterations) during one or more iterations after a change in target ranges. In some embodiments, operation 506 is performed by a processor component the same as or similar to target component 32 (shown in FIG. 1 and described herein).

At an operation 508, the brain activity parameters are compared to the target ranges. In some embodiments, the current sleep stage may be compared to the target sleep stage. In some embodiments, operation 508 is performed by a processor component the same as or similar to comparison component 34 (shown in FIG. 1 and described herein).

At an operation 510, the sensory stimulators are controlled to provide sensory stimulation to the subject. The sensory stimulators are controlled to provide sensory stimulation to the subject to guide the brain activity parameters of the subject into the target ranges. In some embodiments, the sensory stimulators provide sensory stimulation in order to reduce discrepancies between measured brain activity parameters and the target ones. In some embodiments, the sensory stimulators are controlled to provide sensory stimulation to the subject to cause the current sleep stage of the subject to transition to the target sleep stage. In some embodiments, operation 510 is performed by a processor component the same as or similar to control component 36 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

The invention claimed is:

1. A system configured to facilitate transitions between sleep stages during a sleep session of a subject, the system comprising:
one or more sensory stimulators configured to provide sensory stimuli to the subject during the sleep session;
one or more sensors configured to generate output signals conveying information related to brain activity of the subject; and
one or more physical computer processors configured by computer readable instructions to:
determine one or more brain activity parameters of the subject based on the output signals, the one or more brain activity parameters including:
a frequency, an amplitude, and a phase of
a sleep slow wave in the subject;
determine target ranges for the one or more brain activity parameters, the target ranges determined based on one or more of previous sleep sessions of the subject or information received from a user;
compare a given brain activity parameter to a corresponding target range; and
control the sensory stimulators to provide sensory stimulation to the subject to guide the brain activity parameters of the subject into the target ranges such that, responsive to the given brain activity parameter being outside the corresponding target range, the control component controls the sensory stimulators to provide sensory stimulation to the subject to guide the given brain activity parameter into the corresponding target range.

2. The system of claim 1, wherein the one or more physical computer processors are configured such that the one or more brain activity parameters are related to a frequency content of an electroencephalogram.

3. The system of claim 1, wherein the one or more physical computer processors are configured to receive a target sleep stage from the user and determine the target ranges for the brain activity parameters based on the target sleep stage.

4. The system of claim 1, wherein the one or more physical computer processors are configured to determine a current sleep stage of the subject, determine a target sleep stage of the subject, compare the current sleep stage to the target sleep stage, and, responsive to the current sleep stage not matching the target sleep stage, control the sensory stimulators to provide sensory stimulation to the subject to transition the subject from the current sleep stage to the target sleep stage.

5. The system of claim 4, wherein the one or more physical computer processors are configured such that the target sleep stage is a lighter sleep stage relative to the current sleep stage.

6. The system of claim 1, wherein the target ranges are determined based on the previous sleep sessions of the subject, the information received from the user, and information from previous sleep sessions of a population of subjects that are related to the subject.

7. The system of claim 1, wherein the one or more brain activity parameters of the subject further include a density of sleep slow waves, the density of sleep slow waves comprising a number of sleep slow waves that occur in a given period of time.

8. A method for facilitating transitions between sleep stages during a sleep session of a subject with a facilitation system, the system comprising one or more sensory stimulators, one or more sensors, and one or more physical computer processors, the method comprising:
- generating output signals conveying information related to brain activity of the subject with the one or more sensors;
- determining one or more brain activity parameters of the subject based on the output signals with the one or more physical computer processors, the one or more brain activity parameters including:
  - a frequency, an amplitude, and a phase of a sleep slow wave in the subject;
- determining target ranges for the one or more brain activity parameters with the one or more physical computer processors, the target ranges determined based on one or more of previous sleep sessions of the subject or information received from a user;
- comparing a given brain activity parameter to a corresponding target range with the one or more physical computer processors; and
- controlling, with the one or more physical computer processors, the sensory stimulators to provide sensory stimulation to the subject to guide the brain activity parameters of the subject into the target ranges such that, responsive to the given brain activity parameter being outside the corresponding target range, the sensory stimulators are controlled to provide sensory stimulation to the subject to guide the given brain activity parameter into the corresponding target range.

9. The method of claim 8, further comprising determining a current sleep stage of the subject, determining a target sleep stage of the subject, comparing the current sleep stage to the target sleep stage, and, responsive to the current sleep stage not matching the target sleep stage, controlling the sensory stimulators to provide sensory stimulation to the subject to transition the subject from the current sleep stage to the target sleep stage.

10. The method of claim 9, wherein the target sleep stage is a lighter sleep stage relative to the current sleep stage.

11. The method of claim 8, wherein the one or more brain activity parameters are related to a frequency content of an electroencephalogram.

12. The method of claim 8, further comprising receiving a target sleep stage from the user and determining the target ranges for the brain activity parameters based on the target sleep stage.

13. The method of claim 8, wherein the target ranges are determined based on the previous sleep sessions of the subject, the information received from the user, and information from previous sleep sessions of a population of subjects that are related to the subject.

14. The method of claim 8, wherein the one or more brain activity parameters of the subject further include a density of sleep slow waves, the density of sleep slow waves comprising a number of sleep slow waves that occur in a given period of time.

15. A system configured to facilitate transitions between sleep stages during a sleep session of a subject, the system comprising:
- means for providing sensory stimuli to the subject during the sleep session;
- means for generating output signals conveying information related to brain activity of the subject;
- means for determining one or more brain activity parameters of the subject based on the output signals, the one or more brain activity parameters including:
  - a frequency, an amplitude, and a phase of a sleep slow wave in the subject;
- means for determining target ranges for the one or more brain activity parameters, the target ranges determined based on one or more of previous sleep sessions of the subject or information received from a user;
- means for comparing a given brain activity parameter to a corresponding target range; and
- means for controlling the sensory stimulators to provide sensory stimulation to the subject to guide the brain activity parameters of the subject into the target ranges such that, responsive to the given brain activity parameter being outside the corresponding target range, the means for controlling controls the means for providing to provide sensory stimulation to the subject to guide the given brain activity parameter into the corresponding target range.

16. The system of claim 15, wherein the means for determining one or more brain activity parameters is configured such that the one or more brain activity parameters are related to a frequency content of an electroencephalogram.

17. The system of claim 15, wherein the means for determining target ranges is configured to receive a target sleep stage from the user and determine the target ranges for the brain activity parameters based on the target sleep stage.

18. The system of claim 15, wherein the means for determining one or more brain activity parameters is configured to determine a current sleep stage of the subject, wherein the means for determining target ranges is configured to determine a target sleep stage of the subject, wherein the means for comparing is configured to compare the current sleep stage to the target sleep stage, and wherein the means for controlling, responsive to the current sleep stage not matching the target sleep stage, is configured to control the means for providing to provide sensory stimulation to the subject to transition the subject from the current sleep stage to the target sleep stage.

19. The system of claim 18, wherein the means for determining target ranges is configured such that the target sleep stage is a lighter sleep stage relative to the current sleep stage.

20. The system of claim 15, wherein the target ranges are determined based on the previous sleep sessions of the subject, the information received from the user, and information from previous sleep sessions of a population of subjects that are related to the subject.

21. The system of claim 15, wherein the one or more brain activity parameters of the subject further include a density of sleep slow waves, the density of sleep slow waves comprising a number of sleep slow waves that occur in a given period of time.

* * * * *